(12) United States Patent
Wakuda et al.

(10) Patent No.: US 7,052,507 B2
(45) Date of Patent: May 30, 2006

(54) CATHETER WITH BALLOON

(75) Inventors: Hiroshi Wakuda, Otsu (JP); Masato Shimagami, Kusatsu (JP); Yoshiharu Yamazaki, Otsu (JP)

(73) Assignee: Toray Industries, Inc., Tokyo (JP)

( * ) Notice: Subject to any disclaimer, the term of this patent is extended or adjusted under 35 U.S.C. 154(b) by 670 days.

(21) Appl. No.: 10/168,791

(22) PCT Filed: Dec. 21, 2000

(86) PCT No.: PCT/JP00/09068

§ 371 (c)(1),
(2), (4) Date: Jun. 24, 2002

(87) PCT Pub. No.: WO01/47593

PCT Pub. Date: Jul. 5, 2001

(65) Prior Publication Data

US 2002/0193820 A1    Dec. 19, 2002

(30) Foreign Application Priority Data

Dec. 24, 1999  (JP)  ................. 11-366658
Jan. 24, 2000  (JP)  ................. 2000-014566

(51) Int. Cl.
*A61M 29/00*  (2006.01)
(52) U.S. Cl. .............. 606/194; 606/191; 606/192; 604/96.01; 604/104
(58) Field of Classification Search ........ 604/96.01, 604/103.09, 104, 264, 523, 524, 525, 526, 604/527, 917; 606/108, 192, 194, 198, 199
See application file for complete search history.

(56) References Cited

U.S. PATENT DOCUMENTS

| | | | | |
|---|---|---|---|---|
| 5,100,386 A | * | 3/1992 | Inoue ..................... 604/103 |
| 5,201,706 A | * | 4/1993 | Noguchi et al. ....... 604/103.12 |
| 5,334,160 A | * | 8/1994 | Ellis ...................... 604/167.03 |
| 5,397,306 A | * | 3/1995 | Nobuyoshi et al. .... 604/103.14 |
| 5,769,814 A | | 6/1998 | Wijay et al. |
| 5,865,721 A | * | 2/1999 | Andrews et al. .............. 600/18 |
| 2002/0010435 A1 | * | 1/2002 | Sagstetter ................... 604/243 |

FOREIGN PATENT DOCUMENTS

JP    11-347128    * 12/1999

* cited by examiner

*Primary Examiner*—Anhtuan T. Nguyen
*Assistant Examiner*—Robert Lynch
(74) *Attorney, Agent, or Firm*—Nixon & Vanderhye P.C.

(57) ABSTRACT

A catheter with a balloon for mitral valve formative operation includes a double tube having an inner tube and an outer tube disposed concentrically. A balloon is fastened at one end to the inner tube and at the other end to the outer tube. A balloon-extending pipe stopper is disposed at the tip of the inner tube and includes an entry diameter at one end sized to receive a balloon-extending pipe with an allowance. An inner diameter of the balloon-extending pipe stopper at an opposite end is smaller than the entry diameter. The inner diameter of the extending pipe stopper is substantially equivalent to a diameter of the balloon-extending pipe. In use, the balloon-extending pipe is inserted into the inner tube and brought into contact with the balloon-extending pipe stopper for axially extending the balloon for contraction in diameter.

11 Claims, 3 Drawing Sheets

1

CATHETER WITH BALLOON

This application is the U.S. national phase of International PCT Application No. PCT/JP00/09068, filed Dec. 21, 2000, which designated the United States. PCT/JP00/09068 claims priority of Japanese Patent Application No. 1999-366658 filed Dec. 24, 1999, and Japanese Patent Application No. 2000-14566 filed Jan. 24, 2000.

TECHNICAL FIELD

The present invention relates to a catheter with a balloon used for expanding a constricted mitral valve of the heart, to thereby normalize blood flow in a medical management. Particularly it relates to a catheter with a balloon made smaller in the diameter of the tube to be inserted into a blood vessel, smaller in the number of parts and improved in manipulation convenience.

In recent years, the management method using a catheter with a balloon is widely spread. A balloon contracted in diameter is made to get into a constricted or imperforated blood vessel, etc., and a fluid is pressed into the balloon for inflating it, to thereby expand the blood vessel, etc. as a management for normalizing the constricted or imperforated portion. Furthermore, also for non-surgical operational percutaneous commissurotomy to substitute the valve surgical operation for a cardiac valve constricted due to ageing, calcification or aftereffect of rheumatic fever, or the valve replacement operation for an artificial valve, catheters with balloons, for example as described in JP8-2545981B, are already popularly used.

FIG. 3 is a sectional view showing a state in which the balloon of a conventional catheter is inflated, and FIG. 4 is a sectional view showing a state in which the balloon of a conventional catheter is contracted.

In the case of a conventional catheter with a balloon, as shown in FIG. 3, a balloon 52 attached at the tip of a tube 51 is made to get into a blood vessel M together with the tube 51 along a guide wire W and inflated for management. When the balloon 52 is made to get into the blood vessel M or when the balloon 52 is drawn out of the blood vessel M, as shown in FIG. 4, the balloon 52 is extended for being contracted in diameter.

The tube 51 is a double tube consisting of an inner tube 53 and an outer tube 54, and one end of the balloon 52 is fastened on the side of the inner tube 53, while the other end is fastened on the side of the outer tube 54. While the outer tube 54 is kept in position, the inner tube 53 only is pushed by means of an extending pipe 55, to advance relatively to the outer tube 54, for axially extending the balloon 52 for contracting it in diameter.

OBJECTS OF THE INVENTION

However, the above-mentioned catheter with a balloon has a problem that the double tube 51 is thick. If the tube 51 is thick, it is difficult to insert the tube 51 into the blood vessel M.

The reasons why the double tube 51 of the conventional catheter with a balloon is thick are that the diameter of the inner tube 53 must be large to ensure that the extending pipe 55 used for pushing the inner tube 53 can be inserted when the balloon 52 is contracted in diameter, and that the diameter of the outer tube 54 must also be large to ensure that an air-extracting tube 56 can be inserted for extracting the air in the balloon 52.

In view of the above situation, an object of the present invention is to provide a catheter with a balloon that can be made smaller in the diameter of the tube and can also be smaller in the number of parts. Furthermore, in the above-mentioned conventional catheter with a balloon, since the clearance between the inner diameter d3 of the balloon-extending pipe stopper at the tip of the inner tube and the guide wire W is large when the tip of the catheter with a balloon is inserted into the incision of the blood vessel M along the guide wire W, the degree of freedom at the tip position is large, and the guide wire W does not act sufficiently as a guide, making it difficult to insert the tip into the blood vessel M.

In view of the above situation, another object of the present invention is to provide a catheter with a balloon that allows the tip of the catheter with a balloon to be smoothly inserted into the incision of the blood vessel M.

DISCLOSURE OF THE INVENTION

To achieve these and other objects, the present invention relates to a catheter with a balloon, comprising a double tube having an inner tube and an outer tube disposed concentrically and a balloon fastened at one end to the inner tube and at the other end to the outer tube, and further satisfying the following requirement (A) or (B):

(A) Without any air-extracting tube provided between the outer tube and the inner tube, the outer diameter of the outer tube is 4 mm or less, and the average bending moment of the outer tube at 40 cm or less from the tip of the tube at a bending angle of 45 degrees is in a range of 70 to 250 g·cm.

(B) The inner diameter d3 of a balloon-extending pipe stopper provided at the tip of the inner tube is in such a range that the inner diameter d3 is not substantially different in level from the inner diameter d4 of a balloon-extending pipe that is inserted into the inner tube and brought into contact with the balloon-extending pipe stopper for axial extension and radial contraction of the balloon.

MEANINGS OF SYMBOLS

Figure 1:
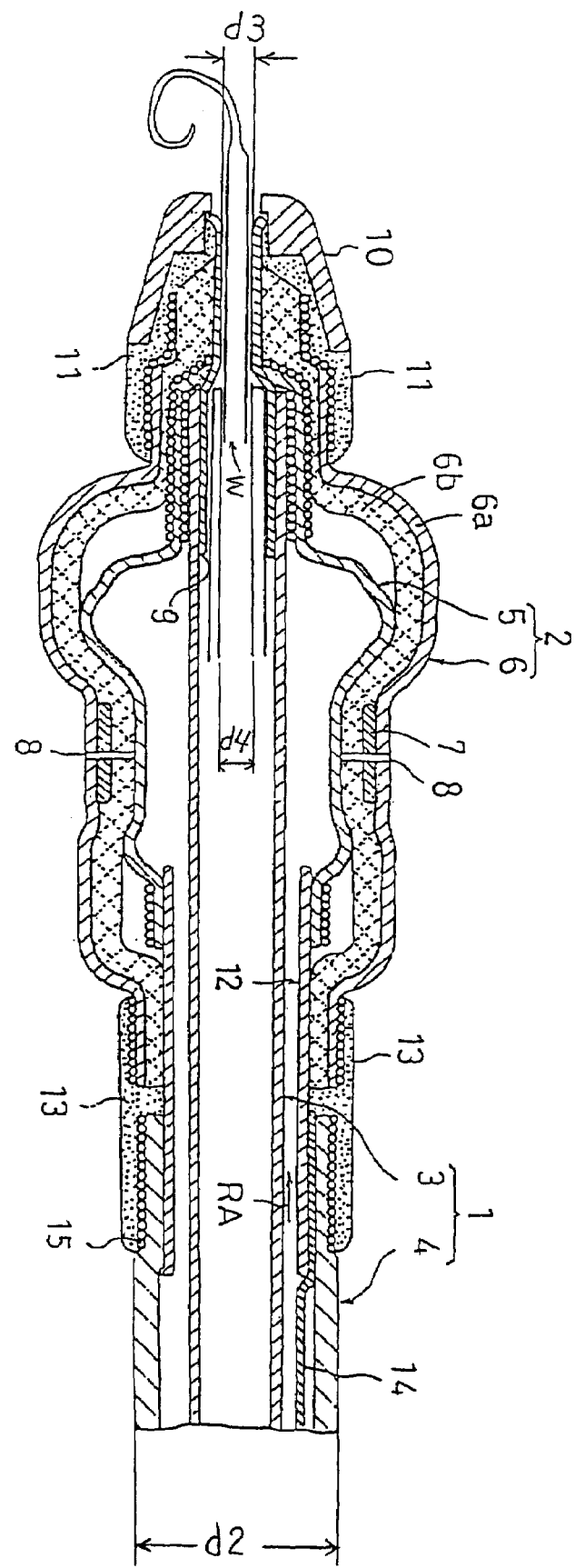
FIG. 1 is a sectional view showing the detailed constitution near the tip of a catheter as an embodiment of the present invention.

1 . . . tube 2 . . . balloon 3 . . . inner tube 4 . . . outer tube 5 . . . inner balloon 6 . . . outer balloon 6a . . . elastic film 6b . . . cylindrical sheath-core yarn 7 . . . band 8 . . . relief hole 9 . . . tip pipe (balloon-elongation pipe stopper) 10 . . . tip 11 . . . adhesive 12 . . . connecting pipe 13 . . . adhesive 14 . . . lead yarn 15 . . . binding yarn 16 . . . manipulation hub of inner tube-sliding needle 17 . . . balloon-extending pipe hub 18 . . . rib 19 . . . Y connector 51 . . . tube 52 . . .

balloon 53 ... inner tube 54 ... outer tube 55 balloon-extending pipe 56 ... air-extracting tube W ... guide wire M ... blood vessel d1 ... length of manipulating hub 16 d2 ... outer diameter of outer tube d3 ... inner diameter of tip pipe d4 ... inner diameter of extending pipe

THE BEST MODES FOR CARRYING OUT THE INVENTION

The action in the case where the balloon of the catheter with a balloon (hereinafter simply called "catheter" as the case may be) of the present invention is extended for radial contraction for insertion into a blood vessel is described below.

When the balloon of the catheter of the present invention is inserted into a duct (blood vessel, etc.) for management, or drawn out of the duct, the inner tube is made to advance relatively to the outer tube, for extending the balloon in the axial direction of the tube for radial contraction.

In the present invention, it is necessary that the average bending moment of the outer tube at 40 cm or less from the tip of the tube at a bending angle of 45 degrees is 70 to 250 g·cm. A preferred range of average bending moment is 90 to 200 g·cm.

For measuring the bending moment, Tinius Olsen Stiffness Tester is used at a span length of 12 mm and a weight of 95 g, and a 50 mm long outer tube sample taken from the position of 2 to 3 mm apart from the bound portion of the connecting pipe toward the operator's side is fastened by about 20 mm in the rotary sample vice. Then, the load scale and the angle indicator are adjusted for the zero point, and the motor engaging lever is turned on, to visually confirm the angle indicator during automatic operation every 5 degrees, while the load scale is observed almost simultaneously, for recording the data till the angle reaches 45 degrees. This measurement is carried out also with other catheters. The average value of three samples at 45 degrees is used to express the bending moment.

The bending moment can be calculated from 95×Indicated value of load scale (%)÷100 (g-cm).

In the present invention, the outer diameter of the outer tube is smaller than that of the conventional outer tube, but since the bending moment at a bending angle of 45 degrees is in a range of 70 to 250 g·cm, the same stiffness as that of the conventional outer tube and the flexibility necessary as a catheter are assured. Furthermore, since the outer diameter of the tube is smaller, it can smoothly move in a blood vessel, to improve the manipulation convenience.

In the present invention in which the requirement (B) is satisfied, on the operator's side of the tip pipe 9, the outside of the extending pipe can be inserted into the inside of the tip pipe 9 with an allowance, but on the tip side, the inner diameter of the tip pipe 9 is so reduced as to be not substantially different in level from the inner diameter of the balloon-extending pipe stopper, for allowing the function as the balloon-extending pipe stopper. Furthermore, when the tip of the extended balloon is inserted into the incision of the blood vessel along the guide wire, the clearance between the outer diameter of the guide wire and the inner diameter of the extending pipe stopper (i.e., the tip of the inner tube) can be kept small, and as a result, the guide wire can guide the tip of the balloon accurately into the incision of the blood vessel. That the inner diameter d3 of the balloon-extending pipe stopper is in such a range that the inner diameter d3 is not substantially different in level from the inner diameter d4 of the balloon-extending pipe means that the difference between both is in a range of about ±0.3 mm, preferably in a range of ±0.2 mm. It is further preferred that the inner diameter d3 of the balloon-extending pipe stopper is within ±0.1 mm of the inner diameter d4 of the balloon-extending pipe.

It is preferred that the balloon of this invention is a double balloon consisting of an inner balloon inflated by means of an introduced fluid and an outer balloon for receiving, on the outside, the inner balloon inflated by means of the introduced fluid. In this case, the double balloon is easy to inflate and hard to break, and has sufficient extensibility and pressure resistance.

As described above, even though the catheter of the present invention is smaller in outer diameter, it can be manipulated with the same sense as felt with the conventional catheter, and allows easy insertion into an incision of a blood vessel. Since the catheter is thinner, the convenience of moving and manipulating it in the blood vessel improves, and the pain of the patient can be reduced while the manipulation convenience of the operator improves.

Furthermore, in the catheter of the present invention, if the balloon is inflated by means of an inflating liquid and contracted once to three times with the balloon kept down, the air in the balloon goes out. So, the air-extracting tube is unnecessary and the space otherwise necessary for it can be eliminated. Therefore, the diameter of the outer tube can be further reduced. In the conventional catheter, for the convenience of inserting the balloon, air is extracted after inserting the balloon into the human body. So, a thin air-extracting tube is necessary. If there exists a thin air-extracting tube, the air in the air-extracting tube cannot be simply extracted even if the balloon is repeatedly inflated by means of the inflating fluid and contracted with the balloon kept down.

Moreover, since there is no substantial level difference between the inner diameter d3 of the extending-pipe stopper and the inner diameter d4 of the balloon-extending pipe, it does not happen that the tip is caught, for allowing smooth operation when the guide wire W is inserted.

Furthermore, it is preferred that the outer diameter of the outer tube is 4 mm or less, that the outer tube is made of a synthetic resin, and that the content of a plasticizer contained in the synthetic resin is 28 parts to 45 parts. Even if the content of $BaSO_4$ (barium sulfate), bismuth carbonate or tungsten, etc. as a contrast medium is kept in a range of 30 parts to 60 parts, there are advantages that the tube with a smaller diameter can have the same flexural stiffness as that of the tube with the conventional diameter, and that the X-ray identifying characteristic improves. If either of these measures is taken, the tube with a smaller diameter can have the same flexural stiffness as that of the tube with the conventional diameter without affecting the manipulation during operation.

In the case where polyvinyl chloride is used as the synthetic resin, a plasticizer contained in the polyvinyl chloride can be selected, for example, from diheptyl phthalate, dioctyl phthalate, dibutyl phthalate, octyldecyl phthalate, diisodecyl phthalate, butylbenzyl phthalate, etc. It is preferred that the content of the plasticizer is 31 parts to 40 parts.

If the balloon has a double balloon structure in which an outer balloon receives an inner balloon inflated by means of an introduced fluid, the balloon is easy to inflate and hard to break, and has sufficient extensibility and pressure resistance.

Furthermore, in the case where a fabric containing sheath-core yarns each consisting of an elastic filament for the core and a non-elastic filament for the sheath larger in free length than the elastic filament for the core is used to reinforce the balloon, the balloon has adequate extensibility, sufficient pressure resistance and inflation uniformity.

If the extended balloon length is 57 to 65 mm between the bundled portions when inserted into a blood vessel without changing the diameter of the expanded balloon, it can pass through the applied sheath 12 Fr (4.0 mm). Since the balloon can be made smaller in diameter when inserted without changing the valve expanding effect, it can pass smoothly in the blood vessel.

Since the outer diameter of the outer tube is 4 mm or less, it can smoothly move in the blood vessel to reduce the pain of the patient and to improve the manipulation convenience of the operator.

To allow the tip of the balloon to be inserted smoothly without injuring the blood vessel, if 3 to 8 ribs are provided inside the tip of the balloon, with the inner diameter of the disposed ribs kept within the maximum outer diameter of the extending pipe stopper +0.3 mm, the ribs act as a guide when the tip is bonded, and the tip is unlikely to incline against the extending pipe stopper, for facilitating the bonding work.

It is preferred that the length of the manipulating hub of the inner tube-sliding needle is 3.6 mm to 10 mm.

If the length of the manipulating hub of the sliding needle is kept as long as 3.6 to 10 mm, it is easy to grasp and hard to slip, and the manipulation convenience improves.

Figure 2:
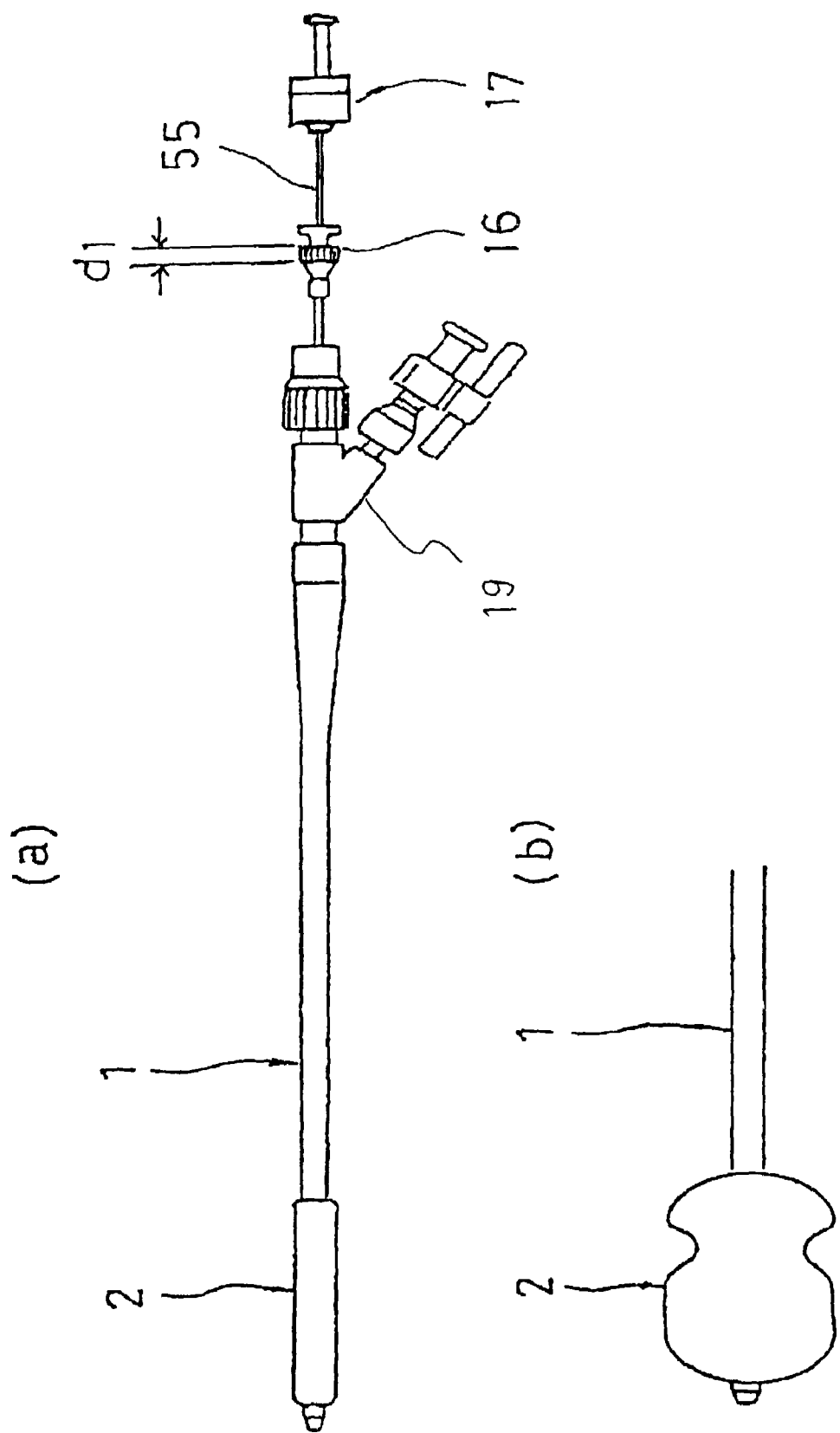
FIG. 2 is a plan view showing the schematic constitution of an entire catheter as an embodiment of the present invention.
Figure 3:
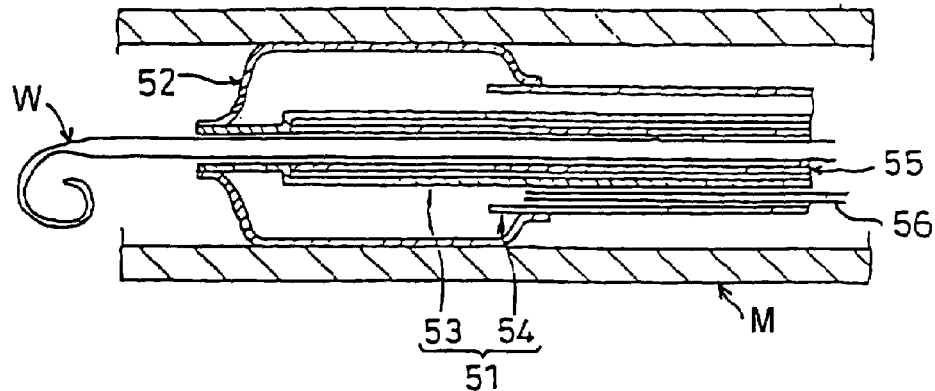
FIG. 3 is a sectional view showing a state where the balloon of a conventional catheter is inflated.
Figure 4:
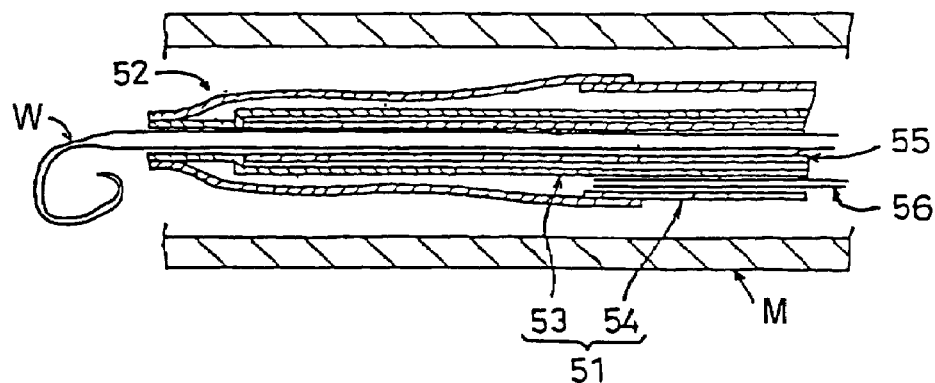
FIG. 4 is a sectional view showing a state where the balloon of a conventional catheter is contracted.

An embodiment of the catheter with a balloon of the present invention is described below more particularly in reference to the drawings. FIG. 1 is a sectional view showing the detailed constitution near the tip of the catheter as an embodiment of the present invention. FIG. 2(a) is a plan view showing the schematic constitution of the entire catheter as an embodiment of the present invention. FIG. 2(b) is a plan view showing the form of an inflated balloon.

The catheter shown as an embodiment in FIG. 2(a) has a slender tube 1 with a round cross section and a smooth surface and a balloon 2 attached to the tip of the tube 1, and furthermore, as required, a fluid inlet, etc. at the rear end of the tube 1.

The tube 1 is, as shown in FIG. 1, a double tube consisting of an inner tube 3 and an outer tube 4 with one inserted in the other concentrically and mutually slidably in the axial direction. The balloon 2 of this example is a double balloon consisting of an inner balloon 5 to be inflated by means of an introduced fluid and an outer balloon 6 for receiving, on the outside, the inner balloon inflated with the introduced fluid.

The inner balloon 5 is a cylindrical elastic film and is coated on both sides with silicone grease. The outer balloon 6 consists of an outer cylindrical elastic film 6a and an inner cylindrical sheath-core yarn fabric 6b for reinforcing the balloon, and the balloon-reinforcing sheath-core yarn fabric 6b is stuck to the inner surface of the elastic film 6a using a rubber cement, etc., to prevent the scattering of the elastic film 6a and to assure uniform inflation without relative shifting even if the balloon is inflated and contracted. The length of the balloon 2 is free, but in most cases, an adequate range is 15 to 70 mm.

As described above, it is desirable that the entire layer structure of the double balloon 2 is a three-layer structure consisting of said elastic film, cylindrical sheath-core yarn fabric and elastic film. The elastic film of the inner balloon 5 effectively reinforced by the outer balloon 6, particularly the sheath-core yarn fabric 6b has sufficient extensibility and pressure resistance (about 2 to 5 atmospheric pressure at which a valve can be mechanically dehisced) and allows a high inner pressure to be achieved in the balloon. The elastic film 6a with a smooth surface acts to contract the expanded balloon and to allow good passage in the blood vessel.

Furthermore, to ensure that the inflated balloon 2 is shaped like a guitar as shown in FIG. 2(b), an elastic band 7 is bonded at about the center of the outer balloon 6 using a rubber cement, etc. The band 7 is placed and bonded between the elastic film 6a and the sheath-core yarn fabric 6b, and since the inflation is inhibited at the place of the band 7 compared with the other places, the balloon 2 is shaped like a guitar. If the band 7 is positioned at the port of the valve to be expanded, the balloon does not slip out of the valve port. Of course, in the case where the balloon is not shaped like a guitar, the elastic band 7 is not necessary.

To avoid a situation in which when the inner balloon 5 inflated by means of the inflating fluid breaks accidentally, the liquid cannot be sucked using a syringe while there is no relief hole for the liquid, not allowing the balloon 2 to be deflated, several thin relief holes 8 are formed in the outer balloon 6. If the balloon 2 remains inflated, the catheter cannot be drawn out of the human body. If the inner balloon 5 breaks, the liquid is discharged from the thin relief holes 8, to automatically deflate (contract) the balloon 2.

The elastic films used in the balloons 5 and 6 are usually highly extensible thin films with smooth surfaces, and the thickness of each film is usually smaller on the tip side than on the rear side. If the thickness on the tip side is smaller than that on the rear side, the balloon is inflated (expanded) on the tip side in the beginning. As the material of the elastic films, polyurethane and rubbers such as latex can be enumerated, and especially a rubber is suitable for the balloons since it is small in initial modulus.

It is preferred that the thickness of an elastic film is in a range of 0.1 to 0.4 mm. It is not necessary that the elastic films used in both the balloons 5 and 6 are equal in thickness. The difference between the thickness on the tip side and that on the rear side can be about 5 to 25%. For example, the cylindrical elastic film can be made thinner in the corresponding portion when manufactured, or as a simpler method, a manufactured cylindrical elastic film can be expanded at the corresponding portion to fix the residual elongation for thinning at the corresponding portion.

On the other hand, the cylindrical sheath-core yarn fabric 6b is made from sheath-core yarns (bicomponent yarns) each consisting of an elastic filament for the core and a non-elastic filament for the sheath larger in free length than the elastic filament for the core, and can be a fabric such as a knitted fabric, woven fabric, nonwoven fabric, braid, or cylinder formed by traverse winding. Above all, an extensible knitting structure is preferred.

It is preferred that the ratio of the free length of the elastic filament for the core to that of the non-elastic filament for the sheath is 0.15 to 0.5. A further preferred range is 0.2 to 0.35. If the value is too large, it is difficult to sufficiently inflate the balloon. If the value is too small, the reinforcing effect of the non-elastic filament is not sufficiently exhibited, and the balloon is likely to break when it is inflated. However, in the case where the sheath-core yarn fabric 6b is produced with sufficient care exercised for avoiding the breaking, even if the ratio is larger, the effect of the present invention can be exhibited.

The ratio of free lengths can be known by measuring the point at which the S—S curve of the sheath-core yarn is bent toward the high tension side. In the case where said bent point is unclear because the free length of the non-elastic filament varies, it can be known by extrapolating from the straight portions on both sides.

A sheath-core yarn has a structure in which an elastic filament is used as the core while a non-elastic filament is used as the sheath. As the case may be, it is practiced that the yarn is expanded and contracted beforehand to acquire inclination, for facilitating the expansion by an internal pressure or for assuring the order of partial expansion or the finally expanded shape. In this case, both the constituent filaments maybe separated to give an adverse effect.

A sheath-core yarn can be made by a method of doubled twisting or fluid entangling, with the non-elastic filament overfed. Especially a sheath-core yarn obtained by spirally winding a synthetic twist yarn (non-elastic filament) around a urethane filament (elastic filament) is preferred since it is compact. It is preferred that the non-elastic filament is a finished yarn, since it is excellent in extensibility, adhesiveness to the elastic film, etc. As the finished yarn, a false twist yarn excellent in extensibility is desirable. If the non-elastic filament is not a finished yarn, separation from the elastic filament is likely to occur disadvantageously. If any measure such as sufficiently increasing the count of twist is taken, the disadvantage of being likely to cause separation can be avoided.

The elastic filament for the core is not especially limited if it is an extensible filament. For example, a single yarn or twist yarn made of a rubber such as natural rubber of synthetic rubber, or polyurethane is adequate, and the synthetic fiber yarn (non-elastic filament) to be wound around the core can be a tenacious yarn of nylon, polyester or polytetrafluoroethylene ("Teflon"), etc., or a highly tenacious yarn of a polyimide or polyethylene, etc. However, a twist yarn is preferred since it is highly bendable. The thicknesses of the yarns are not especially limited since the required pressure resistance depends on the acting region and purpose. However, usually the thickness of the elastic filament for the core is selected in a range of 11 to 56 dtex, and that of the non-elastic filament such as a tenacious yarn or highly tenacious yarn to be wound around the core, 33 to 167 dtex.

Figure 5:
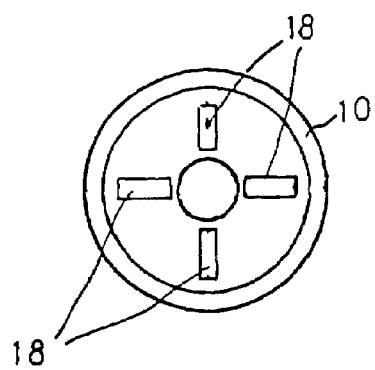
FIG. 5 is a sectional view showing a state of ribs installed inside the tip.

The balloon 2 is, as shown in FIG. 1, fixed at one end on the side of the inner tube 3, and is fixed at the other end on the side of the outer tube 4, to be attached to the double tube 1. That is, a metallic tip pipe 9 is inserted into the tip of the inner tube 3 up to about one half of the entire length of the tip pipe 9, and a yarn 15 is used to bind the inner tube 3 for fastening the metallic tip pipe 9. One end of the inner balloon 5 is bound and fastened by means of a yarn 15 in the region where the tip pipe 9 is inserted, and one end of the outer balloon 6 is also bound and fastened by means of a yarn 15 in the region where the tip pipe 9 is inserted. Furthermore, at the tip end of the double tube 1, a tapered tip 10 is bonded and fastened by means of an adhesive 11 such as an epoxy resin adhesive, and the ends and joints of the balloons are smoothly finished by means of an adhesive 11 such as an epoxy resin adhesive. Inside the tip 10, three to eight ribs 18 (see the sectional view of FIG. 5) are installed. The inner diameter of the disposed ribs 18 is within +0.3 mm of the largest diameter of the tip pipe on the tip side. So, though the tip 10 is likely to change indirection since the adhesive is soft when the tip 10 is bonded, the tip pipe 9 acts as a guide to stabilize the tip 10 in direction, for facilitating the bonding work.

Furthermore, a metallic connecting pipe 12 is inserted into the tip of the outer tube 4 up to about ⅓ of the entire length of the connecting pipe, and a yarn 15 is used to bind the outer tube 4, to fasten the metallic connecting pipe 12. The other end of the inner balloon 5 is bound and fastened to the tip of the connecting pipe 12 by means of a yarn, and the other end of the outer balloon 6 is bound and fastened to about the central portion of the connecting pipe 12 by means of a yarn. The ends and joints of the balloons are smoothly finished by means of an adhesive 13 such as an epoxy resin adhesive.

When the catheter is inserted into or drawn out of a blood vessel or intracardiac cavity, a balloon-extending pipe 55 is brought into contact with the tip pipe (balloon-extending pipe stopper) 9 provided at the tip of the inner tube, and the inner tube 3 is slid to advance in the axial direction relatively to the outer tube 4, to extend both the inner and outer balloons 5 and 6 in the axial direction for radial contraction. In the case of the present invention, the balloon extension length is made longer to make balloon diameter smaller, and the outer diameter of the outer tube 4 is kept as small as 4 mm or less. Furthermore, the tip pipe (balloon-extending pipe stopper) 9 is thinner on the tip side. Therefore, the difference between the inner diameter d3 of the tip pipe 9 and the inner diameter d4 of the balloon-extending pipe 55 is +0.2 mm or less, to eliminate the level difference. As a result, when the guide wire W is inserted, it is not caught. Moreover, since the clearance between the inner diameter of the tip pipe 9 and the guide wire W is small, no deviation occurs between the tip 10 and the guide wire W. So, the manipulation for insertion into an incision of a blood vessel can be easily carried out.

As preparation for axially extending the balloon, the balloon-extending pipe 55 is inserted into the inner tube-sliding needle, and the hub of the inner tube-sliding needle and the hub of the balloon-extending pipe 55 are locked. If the length d1 of the manipulating hub 16 of the inner tube-sliding needle is kept at 3.6 to 10 mm during locking and unlocking work, it can be firmly grasped without finger slipping to facilitate manipulation even if the fingers are wet with blood or the like.

If the balloon 2 is inflated by means of an inflating liquid and contracted once to three times with the balloon 2 kept down, the air in the balloon can be extracted without using an air-extracting tube. So, since the air-extracting tube is unnecessary, the space otherwise necessary for it can be eliminated, allowing the diameter of the outer tube to be reduced.

Since both the inner and outer tubes 3 and 4 can be reduced in diameter as described above, the outer diameter of the double tube 1 (i.e., the outer diameter of the outer tube 4) can be made significantly smaller than that of the conventional tube. It is usually desirable that the outer diameter d2 of the outer tube 4 is 14 Fr (4.7 mm) or less, and 12 Fr (4.0 mm) or less is more desirable. Even if the diameter of the outer tube is made smaller, the flexural stiffness of the outer tube can be kept the same as that of the conventional outer tube to ensure that the manipulation during operation is not adversely affected, if the plasticizer content is kept in a range of 28 parts to 45 parts.

The length of the tube 1 is not specified, since it depends on the age and body dimensions of the patient and the distance from the inserted portion to the place of management. However, a preferred length is in a range of 20 to 120 cm.

Examples of the inner tube 3 having stiffness include tubes made of a synthetic resin such as polyethylene, polytetrafluoroethylene ("Teflon"), polypropylene or nylon. In addition to these tubes, it is possible to use a tube made of polyvinyl chloride resin made stiff by extracting a plasticizer with a solvent, a tube made of a synthetic resin made stiff by exposure to radiation for crosslinking and hardening, a tube made of a synthetic resin made stiff using a smaller amount of a plasticizer, and so on.

On the other hand, the outer tube 4 having a hardness suitable for torque action can also be a tube made of the same material as that of the inner tube 3.

Furthermore, it is preferred to add a contrast medium such as barium sulfate, bismuth compound or metallic powder such as tungsten powder, since it can be helpful for identifying the position in the blood vessel by means of X-ray radiography.

In FIG. 1, a lead yarn (e.g., aramid fiber yarn "Kevler" yarn) 14 with its tip held between the inner surface of the outer tube 4 and the outer surface of the metallic connecting pipe 12 and drawn toward the operator's side is provided for preventing the extension of the outer tube 4 when the inner tube 3 is slid to advance in the axial direction relatively to the outer tube 4 for extending both the inner and outer balloons 5 and 6 in the axial direction. The yarn for preventing the extension of the outer tube 4 is not especially limited in material, and a yarn with a high elastic modulus such as a polyamide yarn is adequate. Furthermore, a knitted fabric can also be used instead of the yarn for preventing the extension of the outer tube 4. The yarn or knitted fabric for preventing the extension of the outer tube 4 may also be embedded in the outer tube 4.

The fluid for inflating the balloon 2 is, as indicated by arrow RA in FIG. 1, is fed into the inner balloon 5 through the clearance between the inner tube 3 and the outer tube 4. The fluid for inflating the balloon 2 can be, for example, a liquid such as physiological salt solution or contrast medium or a gas such as carbonic acid gas. A certain amount of the fluid is pressed in by means of a syringe, etc. If the fluid is sufficiently fed into the inner balloon 5, the balloon 2 is inflated a shape like a guitar as shown in FIG. 2(b).

The double balloon 2 of the catheter of the above-mentioned embodiment can extend greatly to be made smaller in outer diameter, and furthermore the diameter of the double tube 1 can also be made very small. So, the catheter can be inserted into a blood vessel according to a simple Seldinger method. Therefore, the wound for management can be small, and the postoperative measure and management can be simple. Furthermore, the time taken till healing can be very short, to reduce the burdens of the patient and the attendant. Also in the case where the balloon 2 is pressed into an intracardiac cavity, the manipulation for inserting the guide wire and letting it ride on the blood flow is easy, and in addition, the tip of the balloon 2 is also so soft as to preclude the possibility of injuring the inner wall of the blood vessel. So, the manipulation convenience improves. Moreover, the cylindrical films for the balloon and the cylindrical sheath-core yarn fabric for reinforcing the balloon can be simply manufactured and assembled at high yields and at low costs.

An example with a particular constitution in conformity with the catheter of the above-mentioned embodiment is described below.

EXAMPLE 1

A sheath-core yarn (bicomponent yarn) was produced by a method of doubled-twisting a 33 dtex polyurethane yarn (elastic filament for the core) and a 78 dtex-24f false twist polyester yarn (non-elastic filament for the sheath) at 412 T/m with the polyester yarn overfed by 370% in reference to the polyurethane yarn. The ratio of free lengths of both the yarns read from the S—S curve was 0.26.

The sheath-core yarn produced like this was knitted into a cylindrical form using a knitting machine having 50 knitting needles around a cylinder having a diameter of 20 mm, to obtain a cylindrical sheath-core yarn fabric 6b used for the outer balloon 6.

On the other hand, the outer tube 4 used was a 690 mm long 11 Fr polyvinyl chloride tube having an outer diameter of 3.7 mm and an inner diameter of 2.6 mm in the tip straight portion and containing 40 parts of DOP (dioctyl phthalate) and 50% of a contrast medium, and on the hollow side of the outer tube, a 222 dtex polyimide twist yarn was placed along as the lead yarn 14. At the tip of the outer tube, a stainless steel pipe was installed as the metallic connecting pipe 12, and at the rear end, similarly a Y connector 19 was installed. The bending moment of the outer tube on the tip side was 100 g·cm.

The inner tube 3 used was a polyvinyl chloride tube with an outer diameter of 1.7 mm at the tip portion containing 24 parts of DOP (dioctyl phthalate), and a stainless pipe with an outer diameter of 1.53 mm and an inner diameter of 1.13 mm on the inner tube side and an outer diameter of 1.2 mm and an inner diameter of 0.8 mm on the tip side was installed as the metallic tip pipe 9. The inner diameter of the tip pipe on the tip side was not different in level from the inner diameter of the extending pipe 55 within a range of ±0.2 mm. At the rear end of the inner tube, a 30 mm long needle adaptor with an outer diameter of 2.5 mm was set. The tip pipe and the needle adaptor were respectively bound and firmly fastened to the inner tube and the outer tube by means of a 70 μm nylon yarn or a 110 μm nylon yarn respectively. The bending moment of the inner tube 3 was 20 g·cm. The inner tube 3 was at first passed through the Y connector and further inserted into the outer tube 4, and the outer tube 4 was fixed to the Y connector, to prepare the portion destined to be the tube 1 of the catheter.

Then, a 25 mm long rubber tube with a wall thickness of 0.2 mm on the tip side and a wall thickness of 0.3 mm on the rear end side was bound and fastened, as the elastic film of the inner balloon 5, at one end and at the other end to the inner tube 3 and the tip of the outer tube 4 using a 70 μm nylon yarn respectively, and the rubber tube was coated on the surface with a small amount of silicone grease.

Furthermore, at about the center of the sheath-core yarn fabric 6b, a 0.2 mm thick 7 mm long rubber band was stuck as the elastic band 7 using a rubber cement, and further on the outside of it, a rubber tube with a wall thickness of 0.2 mm on the tip side and a wall thickness of 0.3 mm on the rear end side was stuck as the elastic film 6a of the outer balloon 6. It was disposed to cover the inner balloon 5, and adjusted to keep the entire length at 25 mm, being bound and fastened to the inner tube 3 and the outer tube 4 using a 70 μm yarn or a 125 μm yarn respectively. The 125 μm nylon yarn used for binding and fastening to the outer tube had a high tensile strength to preclude the breaking of the yarn when the balloon was expanded. The extra knitted fabric portion and rubber portion were cut off, to prepare the double balloon 2 consisting of the inner balloon 5 and the outer balloon 6.

Subsequently, a two-way cock was attached to the Y connector 19, and both the ends of the balloon 2, the tip and joints were finished smoothly using an epoxy resin adhesive to have an outer diameter of 4.0 mm or less, for completing the catheter with a balloon of Example 1.

A syringe was attached to the completed catheter, and air was extracted and replaced by water. Then, about 5 milliliters of water was injected. The balloon 2 was inflated to about 20 mm at the tip only. Further 18 milliliters of water was injected to inflate the balloon 2 to about 26 mm. Then, water was extracted from the balloon 2, to contract the balloon with the surface kept smooth without any crease.

Furthermore, the guide wire W was passed through, and the needle adaptor of the inner tube 3 was pressed to advance the inner tube 3, for axially extending the balloon 2 from 25 mm to 60 mm. The balloon 2 that had a diameter of about 7 mm contracted to a diameter of about 5 mm. When the needle adaptor was returned to the original position, the diameter of the balloon 2 returned to about 7 mm.

Furthermore, with the balloon 2 kept down, the balloon was inflated with water and contracted one to three times, to confirm that the air of the balloon 2 could be perfectly extracted without using an air-extracting tube.

A clinical application example of the catheter with a balloon is described below. In this clinical application example, the catheter was applied to mitral valve formative operation.

At first, a femoral vein was percutaneously punctured, and a catheter for puncturing an interatrial septum was inserted into the left atrium according to the Brockenbrough method. The catheter for puncturing an interatrial septum was replaced by the guide wire, and a dilator was introduced into the left atrium through it, to dilate the femoral vein and the punctured interatrial septum portion. The dilator was removed, and similarly the balloon 2 of the catheter of Example 1 was introduced into the left atrium. A stilette was used to let it pass through the mitral valve port, and furthermore, the balloon 2 was inflated on the tip side by means of a diluted contrast medium. It was lightly drawn and applied to the valve port to be dehisced. At the position, the balloon 2 was inflated, and the balloon 2 expanded the valve port without slipping off. The commissurotomy including 5 seconds of balloon inflation and contraction could be completed within a short period of time, and the manipulation could be carried out more smoothly than before. Furthermore, there was no side effect, and the postoperative hemorrhage arresting time could be shortened. The postoperative progress was so good that the necessary hospitalization period could be shortened.

The present invention is not limited to the above-mentioned mode, and can also be effected in the following modifications.
(1) The catheter of FIG. 1 is a double balloon, but a catheter with a single balloon can also be a modification of the present invention.
Particularly, a catheter with a multi-layer single balloon in which the elastic film as the inner balloon 5 in FIG. 1 is also bonded to the sheath-core yarn fabric 6b, and a catheter with a single-layer single balloon without the sheath-core yarn fabric 6b can be modifications of the present invention.
(2) In the catheter of FIG. 1, the balloon is inflated into a shape like a guitar. However, a catheter with a balloon that is inflated into a shape unlike a guitar without the elastic band 7 can also be a modification of the present invention.

INDUSTRIAL APPLICABILITY

According to the catheter with a balloon satisfying the requirement (A) of the present invention, even though the outer diameter of the catheter is smaller, the catheter can be manipulated with the same sense as felt with the conventional catheter, and since the catheter is thinner, the manipulation convenience for moving it in the blood vessel improves. Furthermore, since the air of the balloon can be extracted even without using an air-extracting tube, the inner tube and the outer tube can be made smaller in diameter. As a result, the diameter of the double tube becomes sufficiently small, and the catheter can be easily inserted, to allow smooth management. In addition, the pain of the patient can be reduced, and the postoperative progress is also good. Furthermore, the number of necessary parts can be smaller, to assure better manipulation convenience and cost reduction.

According to the catheter with a balloon satisfying the requirement (B) of the present invention, the extending pipe can be inserted into the balloon-extending pipe stopper at the tip of the inner tube since there is a clearance kept between the inside of the extending pipe stopper and the outside of the extending pipe on the balloon inflation side. However, the inner diameter of the balloon-extending pipe stopper at the other end is not substantially different in level from the inner diameter of the extending pipe. So, when the tip of the extended balloon is inserted into the blood vessel along the guide wire, the small clearance between the guide wire and the extending pipe stopper allows the extending pipe stopper to act as a guide, and the tip of the balloon can be easily inserted into the incision of the blood vessel without deviation. The catheter that allows such easy insertion not only allows smooth management but also reduces the pain of the patient, assuring a good postoperative progress.

According to the catheter in one aspect of the invention, even in the case where the outer tube is made smaller in diameter, if the material of the outer tube contains 28 parts to 45 parts of a plasticizer, the tube can have the same flexural stiffness as that of the tube not made smaller in diameter, and the catheter does not affect the manipulation during operation.

According to the catheter in another aspect of the invention, the balloon has such a double structure that the balloon is easy to inflate and hard to break, and the balloon can have sufficient extensibility and pressure resistance. So, the catheter can be smaller in diameter and easier to insert, and since the inner pressure of the inflated balloon is sufficient, the catheter has high manageability.

According to the catheter in yet another aspect of the invention, the balloon is reinforced by a fabric containing sheath-core yarns each consisting of an elastic filament for the core and a non-elastic filament for the sheath having a longer free length than the elastic filament, and the balloon can have adequate extensibility, sufficient pressure resistance and inflation uniformity. So, the catheter can be smaller in diameter and easier to insert. In addition, the inner pressure of the inflated balloon is sufficient, and creases are little likely to be formed on the surface of the contracted balloon. Thus, the catheter is excellent in manageability.

According to the catheter in still another aspect of the invention, since the balloon extension length as inserted in the blood vessel can be 57 to 65 mm between the bound portions without changing the diameter of the expanded balloon, the balloon can pass through the applied sheath 12 Fr (4.0 mm). Since the catheter can be made thinner when inserted without changing the valve expanding effect, it can smoothly pass through the blood vessel.

According to the catheter in another aspect of the invention, three to eight ribs are provided inside the tip at the tip end of the balloon for smooth insertion of the tip end of the balloon into the blood vessel without injuring the blood vessel, and the inner diameter of the disposed ribs is kept within the maximum diameter of the extending pipe stopper +0.3 mm. Therefore, when the tip is bonded, the ribs act as a guide, and the tip is unlikely to incline against the extending pipe stopper. So, the catheter allows easy bonding work.

According to the catheter in yet another aspect of the invention, since the manipulating hub of the sliding needle is elongated to 3.6~10 mm, it can be easily grasped with hand and is less slippery. So, the catheter improves in manipulation convenience.

What is claimed is:

1. A catheter with a balloon for mitral valve formative operation, comprising a double tube having an inner tube and an outer tube disposed concentrically and a balloon fastened at one end to the inner tube and at the other end to the outer tube, wherein a balloon-extending pipe stopper is provided at a tip of said inner tube, the balloon-extending pipe stopper having an entry diameter sized to receive a balloon-extending pipe with an allowance and tapering at an opposite end to an inner diameter, wherein the inner diameter d3 of the extending pipe stopper is not substantially different from an inner diameter d4 of the balloon-extending pipe that is inserted into the inner tube, and brought into contact with the balloon-extending pipe stopper for axially extending the balloon for contraction in diameter.

2. A catheter with a balloon, according to claim 1, wherein the range in which the inner diameter d3 of the balloon-extending pipe stopper is not substantially different from the inner diameter d4 of the balloon-extending pipe is a range of ±0.2 mm of the inner diameter of the balloon-extending pipe.

3. A catheter with a balloon, according to claim 1, wherein the outer tube is made of a synthetic resin, and the plasticizer content of the synthetic resin is 28 parts to 45 parts.

4. A catheter with a balloon, according to claim 1, said catheter being without any air-extracting tube provided between the outer tube and the inner tube, wherein the outer diameter of the outer tube is 4 mm or less, and wherein the average bending moment of the outer tube at 40 cm or less from the tip of the tube at a bending angle of 45 degrees is in a range of 70 to 250 g·cm.

5. A catheter with a balloon, according to claim 1, wherein the balloon is a double balloon having an inner balloon inflated by means of an introduced fluid and an outer balloon for receiving, on the outside, the inner balloon inflated with the introduced fluid.

6. A catheter with a balloon, according to claim 1, wherein the balloon is reinforced by a fabric containing sheath-core yarns each having an elastic filament for the core and a non-elastic filament for the sheath with a longer free length than the elastic filament for the core.

7. A catheter with a balloon, according to claim 1, wherein the length of the extended balloon between the bound portions is 57 to 65 mm.

8. A catheter with a balloon, according to claim 1, wherein three to eight ribs are provided inside the tip at the tip end of the balloon, and wherein the inner diameter of the disposed ribs is within a maximum outer diameter of the balloon-extending pipe stopper +0.3 mm.

9. A catheter with a balloon, according to claim 1, wherein the length of a manipulating hub of an inner tube-sliding needle is 3.6 mm to 10 mm.

10. A catheter with a balloon, according to claim 1, wherein the outer diameter of the outer tube is 4 mm or less.

11. A catheter with a balloon for mitral valve formative operation comprising:
   a double tube having an inner tube and an outer tube disposed concentrically;
   a balloon fastened at one end to the inner tube and at the other end to the outer tube; and
   a balloon-extending pipe stopper disposed at a tip of the inner tube, the balloon-extending pipe stopper having an entry diameter at one end sized to receive a balloon-extending pipe with an allowance and an inner diameter at an opposite end smaller than the entry diameter,
   wherein the inner diameter of the extending pipe stopper is substantially equivalent to a diameter of the balloon-extending pipe, the balloon-extending pipe being inserted into the inner tube and brought into contact with the balloon-extending pipe stopper for axially extending the balloon for contraction in diameter.

* * * * *